(12) United States Patent
Tanaka et al.

(10) Patent No.: US 6,653,399 B2
(45) Date of Patent: Nov. 25, 2003

(54) WATER ABSORBENT MATERIAL

(75) Inventors: Hisakazu Tanaka, Osaka (JP); Shigeki Ideguchi, Osaka (JP); Yoshiki Hasegawa, Nishinomiya (JP)

(73) Assignee: Dainippon Ink and Chemicals, Inc., Tokyo (JP)

( * ) Notice: Subject to any disclaimer, the term of this patent is extended or adjusted under 35 U.S.C. 154(b) by 66 days.

(21) Appl. No.: 10/082,226

(22) Filed: Feb. 26, 2002

(65) Prior Publication Data
US 2002/0161110 A1 Oct. 31, 2002

(30) Foreign Application Priority Data
Feb. 28, 2001 (JP) ...................... P2001-054417

(51) Int. Cl.[7] .................. C08G 63/19; C08G 69/08
(52) U.S. Cl. .................. 525/54.2; 528/312; 528/313; 528/315; 528/617; 528/322; 528/328; 525/54.21; 525/54.23; 525/54.24; 525/54.3; 524/742; 524/755; 524/777; 522/24; 522/25; 522/27; 522/29
(58) Field of Search .................. 528/312, 313, 528/315, 317, 322, 328; 525/54.2, 54.21, 54.23, 54.24, 54.3; 524/742, 755, 777; 522/24, 25, 27, 29

(56) References Cited

U.S. PATENT DOCUMENTS

| 5,247,068 | A | * | 9/1993 | Donachy et al. ............ 530/350 |
| 5,284,936 | A | * | 2/1994 | Donachy et al. ............ 530/350 |
| 5,461,085 | A | * | 10/1995 | Nagatomo et al. .......... 521/183 |
| 5,525,682 | A | * | 6/1996 | Nagatomo et al. .......... 525/420 |
| 5,612,384 | A | * | 3/1997 | Ross et al. .................... 521/64 |
| 5,801,116 | A | * | 9/1998 | Cottrell et al. .............. 502/404 |
| 5,847,013 | A | * | 12/1998 | Ross et al. .................... 521/64 |
| 5,955,549 | A | * | 9/1999 | Chang et al. ................ 525/418 |
| 5,985,944 | A | * | 11/1999 | Ishizaki et al. ................ 521/64 |
| 5,998,492 | A | * | 12/1999 | Haar, Jr. et al. .............. 521/64 |
| 6,072,024 | A | * | 6/2000 | Irizato et al. ................ 528/328 |
| 6,251,960 | B1 | * | 6/2001 | Ishizaki et al. ................ 521/72 |
| 6,346,569 | B1 | * | 2/2002 | Irizato et al. ................ 524/538 |

FOREIGN PATENT DOCUMENTS

| JP | 2000-239330 | 9/2000 |
| JP | 2000-290370 | 10/2000 |
| WO | WO 99/37624 | 7/1999 |

OTHER PUBLICATIONS

T. Kakuchi et al.; Macromol Rapid Commun., vol. 20, No. 8, pp. 410–414, 1999.

C. J. Chang et al.; Polym. Mater Sci. Eng. No. 79, pp. 232–233, 1998.

* cited by examiner

Primary Examiner—Samuel A. Acquah
(74) Attorney, Agent, or Firm—Armstrong, Westerman & Hattori, LLP

(57) ABSTRACT

A water absorbent material, comprising, as a main component, a water absorbent resin which has a structure in which a anhydropolyamino acid having an ethylenically unsaturated double bond is grafted with polysaccharides, wherein at least a portion of the anhydropolyamino acid is hydrolyzed and crosslinked, has high water absorbency and high biodegradability even if the anhydropolyamino acid has a low molecular weight.

8 Claims, No Drawings

WATER ABSORBENT MATERIAL

BACKGROUND OF THE INVENTION

1. Field of the Invention

The present invention relates to a novel and useful water absorbent material, a method for producing the same, and a water absorbent article using the water absorbent material. More particularly, it relates to a water absorbent material for absorption of high concentration salt-containing solutions such as blood and body fluids, including water, a method for producing the same, and a water absorbent article using the water absorbent material.

The water absorbent material of the present invention can be employed in various fields such as for disposable sanitary material products (for example, paper diapers and sanitary products), household articles, sealing materials, humectants in agricultural products for soil conditioning, anti-condensation coating, water-storing materials in agriculture/horticulture, chemical absorbents and also in the fields in transportation of fresh food or seafood.

2. Description of Related Art

As the water absorbent material, a crosslinked polyacrylic acid (salt) has hitherto been used. Since the crosslinked polyacrylic acid (salt) cannot be easily decomposed into a lower-molecular weight compound, there have arisen problems in the disposal of paper diapers and sanitary products that use a large amount of the crosslinked polyacrylic acid (salt) with the increase in the sense of global environmental protection.

Therefore, as a polymer material having both high water absorbency and excellent biodegradability, a polyamino acid resin having the same molecular structure as that of the polyacrylic acid (salt) has attracted interest as a material to replace the polyacrylic acid (salt). As such a material, for example, water absorbent resins such as polyaspartic acid, polyglutamic acid, and polylysine are known. Among these, a polyaspartic acid water absorbent resin has attracted special interest because it can be prepared by a chemical polymerization method.

As the polyaspartic acid water absorbent resin, for example, there are disclosed (1) water absorbent resin obtained by hydrolyzing a partially crosslinked compound using polyaspartic acid polyamine (WO99/37624), (2) water absorbent resin wherein a crosslinking agent is a diepoxy compound such as ethylene glycol glycidyl ether (Polym. Mater. Sci. Eng., 79, 232, 1998), (3) crosslinked polysuccinimide derivative obtained by reacting a reaction product of a polysuccinimide derivative and an isocyanate having an ethylenically unsaturated bond with a compound having two or more ethylenically unsaturated bonds in the presence of a polymerization initiator (Japanese Patent Application, First Publication No. 2000-239330, Macromol. Rapid. Commun. 20, 410, 1999), and (4) resin obtained by hydrolyzing a reaction product of a polyamino acid and polysaccharides (Japanese Patent Application, First Publication No. 2000-290370).

Among those obtained conventionally as described above, (1) the water absorbent resin using polyaspartic acid polyamine, (2) the water absorbent resin obtained by crosslinking using a diepoxy compound, and (3) the crosslinked polysuccinimide derivative obtained by reacting a reaction product of a polysuccinimide derivative and an isocyanate having an ethylenically unsaturated bond with a compound having two or more ethylenically unsaturated bonds in the presence of a polymerization initiator have satisfactory biodegradability but are insufficient in water absorption properties. To obtain sufficient water absorption properties suited for practical use, it was indispensable to increase the molecular weight of polyaspartic acid. With respect to (4) the resin obtained by hydrolyzing a reaction product of a polyamino acid and polysaccharides, high concentration of a crosslinking agent is required to impart the water absorption properties. Therefore, the crosslink density becomes too high to obtain sufficient water absorption properties, and moreover, the biodegradability is not sufficient.

As described above, conventionally, a resin composition, which has both high water absorbency and excellent biodegradability, cannot at present be obtained at a low price without passing through complicated steps.

BRIEF SUMMARY OF THE INVENTION

An object of the present invention is to provide a water absorbent material having high water absorbency regardless of a acidic anhydropolyamino acid having a low molecular weight, a method for producing the same, and a water absorbent article using the water absorbent material.

The present inventors have intensively researched to achieve the object described above, and thus the present invention has been completed.

The present invention provides a water absorbent material comprising, as a main component, a water absorbent resin which has a structure in which a anhydropolyamino acid having an ethylenically unsaturated double bond is grafted with polysaccharides, wherein at least a portion of the anhydropolyamino acid is hydrolyzed and crosslinked.

The present invention also provides a method for producing a water absorbent material comprising a water absorbent resin as a main component, which comprises reacting a anhydropolyamino acid having an ethylenically unsaturated double bond (A) with polysaccharides (B), crosslinking the reaction product with a crosslinking agent (C), and hydrolyzing at least a portion of constituent components of the anhydropolyamino acid.

The present invention also provides a water absorbent article comprising a liquid permeable sheet, a liquid impermeable sheet, and a water absorber containing a water absorbent material and a fiber material, which is formed between the liquid permeable sheet and the liquid impermeable sheet, wherein the water absorbent material used is a water absorbent material comprising, as a main component, a water absorbent resin which has a structure in which a anhydropolyamino acid having an ethylenically unsaturated double bond is grafted with polysaccharides, wherein at least a portion of the anhydropolyamino acid is hydrolyzed and crosslinked.

According to the present invention, it is made possible to provide a anhydropolyamino acid water absorbent material having high water absorbency and high biodegradability in spite of a low molecular weight. The water absorbent material obtained by the present invention can be employed in various fields such as for disposable sanitary material products (for example, paper diapers and sanitary products), household articles, sealing materials, humectants in agricultural products for soil conditioning, anti-condensation coating, water-storing materials in agriculture/horticulture, chemical absorbents and also in the fields in transportation of fresh food or seafood.

DETAILED DESCRIPTION OF THE INVENTION

The water absorbent material, the method for producing the same, and the water absorbent article using the same will now be described in detail.

First, the water absorbent material comprising, as a main component, a water absorbent resin which has a structure in which a anhydropolyamino acid having an ethylenically unsaturated double bond is grafted with polysaccharides, wherein at least a portion of the anhydropolyamino acid is hydrolyzed and crosslinked, will be described.

The water absorbent resin used in the water absorbent material of the present invention is obtained by graft bonding of the ethylenically unsaturated double bond of the anhydropolyamino acid having an ethylenically unsaturated double bond (A) with the polysaccharides (B), substantially crosslinking the resulting graft compounds with a crosslinking agent (C) and hydrolyzing at least a portion of the anhydropolyamino acid.

As the anhydropolyamino acid having an ethylenically unsaturated double bond (A), for example, those prepared by reacting a anhydropolyamino acid (D) with a compound (E) which has an ethylenically unsaturated double bond and a functional group having a reactivity with the anhydropolyamino acid (D) (hereinafter referred to as a double bond-containing compound (E)) and imide polysuccinate having a maleimide terminal group as a terminal group can be used. The imide polysuccinate having a maleimide terminal group includes, for example, those prepared by the polycondensation reaction with maleic anhydride, fumaric acid or malic acid while heating.

The anhydropolyamino acid (D) does not substantially have an ethylenically unsaturated double bond, but may have some ethylenically unsaturated double bonds, and examples thereof include anhydrides of polyaspartic acid and polyglutamic acid. Among these, imide polysuccinate as an anhydride of polyaspartic acid is preferred because it is easily available. These compounds may be those having a linear structure or those having a branched structure. They may have an amino acid unit other than units of glutamic acid and aspartic acid in a basic skeleton of the anhydropolyamino acid (D).

Examples of the amino acid unit other than units of glutamic acid and aspartic acid include units of amino acids, for example, aliphatic α-amino acid such as glycine, alanine, valine, leucine, isoleucine, serine, threonine, asparagine, glutamine, lysine, ornithine, cysteine, cystine, methionine, proline, hydroxyproline, or arginine; aromatic α-amino acid such as tyrosine, phenylalanine, triptophan, or histidine; those wherein side chain functional groups of these α-amino acids are substituted; aminocarboxylic acid such as β-alanine or γ-aminobutyric acid; dipeptide (dimer) such as glycylglycine or aspartylphenylalanine; and tripeptide (trimer) such as glutathione. These amino acids may be optically active substance (L-compound, D-compound) or racemic modifications. These amino acid units may exist in the form of a random copolymer or a block copolymer after being bonded with glutamic acid or aspartic acid.

The method for preparing the anhydropolyamino acid (D) is not specifically limited. Examples of the method include (i) method of preparing D/L-aspartic acid by dehydration condensation with heating, (ii) method of preparing D/L-aspartic acid by dehydration condensation with heating in the presence of a catalyst such as phosphoric acid, (iii) method of preparing D/L-aspartic acid by dehydration condensation with heating in a proper solvent in the presence of a catalyst such as phosphoric acid, (iv) a method of preparing from maleimide or maleamide acid by heating maleic anhydride, fumaric acid or malic acid with ammonia, and (v) method of preparing by heating maleic anhydride, fumaric acid or malic acid with ammonia to form maleimide or maleamide acid in the presence of a catalyst such as phosphoric acid. As the water absorbent material of the present invention, the anhydropolyamino acid obtained by any method can be used.

The double bond-containing compound (E) is preferably a compound represented by the following general formula (1) in view of the reactivity.

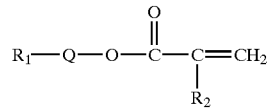

General Formula (1)

wherein $R_1$ represents at least one functional group selected from the group consisting of amino groups, epoxy groups, carboxyl groups, carbodiimide groups, oxazoline groups, imino groups, and isocyanate groups, Q represents an alkylene group having 1 to 10 carbon atoms, and $R_2$ represents hydrogen or an alkyl group having 1 to 4 carbon atoms.

Examples of the compound represented by the general formula (1) include glycidyl methacrylate, glycidyl acrylate, acrylic acid, methacrylic acid, 2-methacryloyloxyethyl isocyanate, and 2-isocyanatomethyl acrylate.

In the present invention, the method of preparing the anhydropolyamino acid having an ethylenically unsaturated double bond (A) includes, for example, a method for reaction between a anhydropolyamino acid (D) and a double bond-containing compound (E). Examples thereof include (i) method of directly adding double bond-containing compound (E) to a powdered anhydropolyamino acid (D), followed by mixing, (ii) method of dispersing a powdered anhydropolyamino acid (D) in an inert solvent and adding a double bond-containing compound (E) to the dispersion, followed by mixing, (iii) method of previously dissolving a anhydropolyamino acid (D) in an aprotic organic solvent such as dimethylformamide, dimethylacetamide, N-methyl-2-pyrrolidone, N,N'-dimethylimidazolinone, dimethyl sulfoxide, or sulfolane and adding a double bond-containing compound (E) to the solution, followed by mixing, (iv) method of adding an aqueous alkali solution to a anhydropolyamino acid (D), thereby to hydrolyze the anhydropolyamino acid (D) and adding a double bond-containing compound (E) to the resulting aqueous solution, followed by mixing, and (v) method of adding an aqueous alkali solution to a anhydropolyamino acid (D), thereby to hydrolyze the anhydropolyamino acid (D), adding an acid to the resulting aqueous solution, thereby to neutralize the hydrolyzate of the anhydropolyamino acid (D), and directly adding a compound which has a functional group having a reactivity with a anhydropolyamino acid, or a hydrolyzate of the anhydropolyamino acid, followed by mixing.

In any method described above, an operation of adding a radical polymerization inhibitor such as hydroquinone or inhibiting the polymerization of the double bond-containing compound (E) by introducing air may be used, if necessary.

The amount of the double bond-containing compound (E) to be used relative to the anhydropolyamino acid (D) is preferably within a range from 0.8 to 3 mol, and more preferably from 0.9 to 2 mol, per mol of the anhydropolyamino acid (D).

When the amount of the double bond-containing compound (E) to be used relative to the anhydropolyamino acid (D) is within the above range, the amount of the unreacted substance can be reduced, thus making it possible to reduce the amount of the substance eluted in water and to inhibit the water absorbency from being lowered. Therefore, it is preferred.

The temperature of the reaction between the anhydropolyamino acid (D) and the double bond-containing compound (E) is not specifically limited, but is preferably within a range from 20 to 150° C.

The molecular weight of the resulting anhydropolyamino acid having an ethylenically unsaturated double bond (A) used in the present invention is preferably 500 or more, and 1000 or more, in terms of a weight-average molecular weight. When the weight-average molecular weight is 500 or more, the objective water absorbent material of the present invention having a sufficiently enhanced water absorbency of water containing salts can be obtained.

A portion or all of the anhydropolyamino acid (D) may be hydrolyzed before reacting with the double bond-containing compound (E).

The hydrolysis reaction of the anhydropolyamino acid (D) is usually conducted by adding an aqueous alkali solution and the reaction temperature is preferably within a range from 0 to 100° C., and more preferably from 20 to 95° C.

The aqueous alkali solution used in the hydrolysis reaction of the anhydropolyamino acid (D) is preferably an aqueous solution of an alkali metal compound and/or an alkali earth metal compound. Among these compounds, a hydroxide or carbonate or a mixture of two or more kinds thereof is preferred and examples thereof include lithium hydroxide, sodium hydroxide, potassium hydroxide, magnesium hydroxide, calcium hydroxide, lithium carbonate, sodium carbonate, potassium carbonate, magnesium carbonate, and calcium carbonate. Particularly, an aqueous solution of sodium hydroxide or potassium hydroxide (0.1 to 40% by weight) is preferably used. The amount of the alkali is preferably within a range from 0.4 to 1.0 mol based on 1 mol of the imide ring group.

For the purpose of adjusting the pH after previously hydrolyzing, the anhydropolyamino acid (D) may be neutralized with a protonic acid such as hydrochloric acid, sulfuric acid, or phosphoric acid. The adjustment of the pH makes it possible to inhibit the hydrolysis of an ester moiety of the double bond-containing compound (E) caused during the reaction between the anhydropolyamino acid (D) and the double bond-containing compound (E).

The water absorbent resin as a main component of the water absorbent material of the present invention is obtained by grafting the ethylenically unsaturated double bond of the anhydropolyamino acid having an ethylenically unsaturated double bond (A) with the polysaccharides (B), followed by crosslinking. Sometimes, the polysaccharides (B) are grafted with the anhydropolyamino acid having an ethylenically unsaturated double bond (A), or a anhydropolyamino acid having a plurality of ethylenically unsaturated double bond (A).

In the water absorbent material of the present invention, by using the polysaccharides (B) as the reaction raw material, a high nonionic moiety is introduced, thus making it possible to impart high water absorbency to water containing salts.

Examples of the method of grafting the polysaccharides (B) with the anhydropolyamino acid having an ethylenically unsaturated double bond (A) include (1) method of grafting a anhydropolyamino acid having an ethylenically unsaturated double bond (A) with polysaccharides (B) in the presence of a redox catalyst, (2) method of adding carbon disulfide to polysaccharides to form a graft point, (3) method of adding a double bond by the esterification reaction between maleic anhydride and polysaccharides and reacting with the resulting compound, (4) method of grafting by kneading polysaccharides with a anhydropolyamino acid having an ethylenically unsaturated double bond (A) with heating, (5) method of using a crosslinking agent capable of reacting with each functional group of a anhydropolyamino acid having an ethylenically unsaturated double bond (A) and/or polysaccharides (B), and (6) method of dissolving or suspending a mixture of a anhydropolyamino acid having an ethylenically unsaturated double bond (A) and polysaccharides (B) in water and usually crosslinking at room temperature under normal pressure by irradiation with radiation such as α-rays, β-rays, γ-rays, electron beams, neutron beams, X-rays, and valence electron beams (γ-rays are preferably used and the γ-ray absorption amount is preferably from 1 to 500 KGy, and the reaction is preferably conducted in an inert gas such as nitrogen or argon). Among these methods, the method of grafting a anhydropolyamino acid having an ethylenically unsaturated double bond (A) with polysaccharides (B) in the presence of a redox catalyst is industrially preferred.

Examples of the polysaccharides (B) include starch, cellulose, and alginic acid.

The starch generally includes starch made of natural amylose and/or amylopectin or those originating in plants, starch-containing substances, and modified substances thereof. Examples thereof include potato starch, cornstarch, wheat starch, tapioca starch, rice starch, sweet potato starch, sago starch, waxy cornstarch, high-amylose cornstarch, wheat flour, and rice flour. As the modified starch, for example, those obtained by graft copolymerization of the starch with a monomer such as acrylate ester, methacrylate ester, olefin, or styrene, those obtained by reacting the starch with fatty acid, and those obtained by gelatinization, oxidation, acid treatment, pregelatinization, etherification, esterification, or crosslinking of the starch can be used. In addition to those, a structure-modified starch may be obtained by heating a moisture-containing starch to a temperature higher than the glass transition temperature and the melting temperature (described in EP-A-327505). Furthermore, polysaccharides such as guar gum, chitin, chitosan, cellulose, alginic acid, and agar can be used.

Examples of the cellulose include cellulose obtained from wood, leaves, stems, basts, and seed fibers; and processed cellulose such as alkyl-etherified cellulose, organic acid-esterified cellulose, carboxymethylated cellulose, cellulose oxide, or hydroxyalkyl-etherified cellulose.

The amount of the polysaccharides (B), a weight ratio of the polysaccharides (B) to the anhydropolyamino acid having an ethylenically unsaturated double bond (A), (B)/(A), is preferably within a range from 0.01/1 to 10/1, and more preferably from 0.1/1 to 5/1. By using the polysaccharides (B) in the amount within the above range, high absorbency can be imparted to the desired anhydropolyamino acid of the present invention having a low molecular weight.

The crosslinking reaction by a crosslinking agent (C) using a reaction product obtained by reacting the anhydropolyamino acid having an ethylenically unsaturated double bond (A) with the polysaccharides (B) in the presence of a redox catalyst will now be described.

The crosslinking agent (C) can be appropriately selected according to the molecular weight of the anhydropolyamino acid (D) and the kind of the polysaccharides (B).

Examples of the crosslinking agent (C) include epoxy crosslinking agent, polyamine crosslinking agent, oxazoline crosslinking agent, aziridine crosslinking agent, carbodiimide crosslinking agent, and isocyanate crosslinking agent.

Examples of the epoxy crosslinking agent include ethylene glycol diglycidyl ether, propylene glycol diglycidyl ether, glycerin-1,3-diglycidyl ether, polyethylene glycol diglycidyl ether, and bisphenol A-epichlorohydrin type epoxy resin.

Examples of the polyamine crosslinking agent include chain aliphatic polyamine such as ethylenediamine, diethylenetriamine, triethylenetetramine, tetraethylenepentamine, pentaethylenehexamine, hexamethylenediamine, or polyether polyamine; cyclic aliphatic polyamine such as menthenediamine, isophoronediamine, or bis(4-aminocyclohexyl)methane-3,9-bis(3-aminopropyl)-2,4,8,10-tetraoxanepyro[5,5]undecane; aromatic polyamine such as m-xylenediamine or p-xylenediamine; polyamides obtained from dimer acid and aliphatic polyamine; and basic amino acid such as lysine.

Examples of the oxazoline crosslinking agent include 2,2'-bis(2-oxazoline), 2,2'-bis(3-methyl-2-oxazoline), 1,4-bis(2-(4-methyl-5-phenyloxazoline))benzene, 2,2'-(1,4-phenylene)-bis(2-oxazoline), and 2,2'-(1,3-phenylene)-bis (2-oxazoline).

Examples of the aziridine crosslinking agent include 2,2-bishydroxymethylbutanol-tris[3-(1-aziridinyl) propionate], diphenylmethane-bis-4,4-N,N'-ethylene urea, hexamethylene-bis-ω,ω-N,N'-ethylene urea, tetramethylene-bis-N,N'-ethylene urea, triphenylmethane-4,4',4"-tetramethylene-bis-N,N'-ethyleneurea, p-phenylenebisethylene urea, m-toluylene-bis-N,N'-ethylene urea, carbonylbisaziridine, a methyl derivative thereof, and 2-(1-aziridinyl)ethyl-methacrylate and a copolymer thereof.

Examples of the carbodiimide crosslinking agent are hydrophilic group-containing or hydrophilic group-free carbodiimide compounds including dicyclohexylcarbodiimide, diphenylcarbodiimide and di-(diisopropyl) phenylcarbodiimide, as well as a so-called isocyanate group-containing carbodiimide compound represented by the following general formula (2):

OCN—$R_5$—(N=C=N—$R_5$)$_n$—NCO     General Formula (2)

(wherein $R_5$ represents an aromatic or aliphatic divalent linking group),
and a so-called isocyanate group-free compound derived from a compound represented by the general formula (2), which is represented by the following general formula (3):

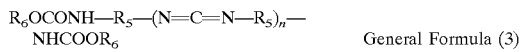

$R_6$OCONH—$R_5$—(N=C=N—$R_5$)$_n$—NHCOOR$_6$     General Formula (3)

(wherein $R_5$ represents an aromatic or aliphatic divalent linking group, and $R_6$ represents an alkyl group, an aralkyl group or an oxyalkylene group).

Examples of the isocyanate crosslinking agent include tolylene diisocyanate (TDI), phenylene diisocyanate (PPDI), diphenylmethane diisocyanate (MDI), hydrogenated MDI, polymeric MDI, tolidinediisocyanate (TODI), hexamethylene diisocyanate (HDI), isophorone diisocyanate (IPDI), xylylene diisocyanate (XDI), lysine diisocyanate (LDI), tetramethylenexylene diisocyanate (TMXDI), triphenylmethane triisocyanate, tris(isocyanatephenyl) thiophosphate, undecane triisocyanate, lysine ester triisocyanate, 1,8-diisocyanate-4-isocyanatemethyloctane, dicyclopentane triisocyanate, urethane-modified compounds, allophanate-modified compounds, burette-modified compounds, isocyanurate-modified compounds, carbodiimide-modified compounds, and block isocyanates, and mixtures thereof.

These crosslinking agents (C) may be used alone, or two or more kinds thereof may used in combination.

In the case in which a anhydropolyamino acid having an ethylenically unsaturated double bond (A) is reacted with polysaccharides (B) in the presence of a redox catalyst, by using, as a crosslinking agent (C), a compound having two or more ethylenically unsaturated bonds, the reaction between the anhydropolyamino acid having an ethylenically unsaturated double bond (A) and the polysaccharides (B) and the reaction with the crosslinking agent (C) can be conducted at the same time.

Examples of the compound having two or more ethylenically unsaturated bonds as the crosslinking agent (C) include acrylic anhydride, methacrylic anhydride, ethylene glycol dimethacrylate, diethylene glycol dimethacrylate, triethylene glycol dimethacrylate, polyethylene glycol dimethacrylate, 1,6-hexanediol dimethacrylate, 2-hydroxy-1,3-dimethacryloxypropane, 2,2-bis[4-(methacryloxyethoxy)phenyl]propane, 2,2-bis[4-(methacryloxypolyethoxy)phenyl]propane, polypropylene glycol dimethacrylate, polyethylene glycol diacrylate, 1,6-hexanediol diacrylate, polypropylene glycol diacrylate, 2,2-bis[4-(acryloxyethoxy)phenyl]propane, 2-hydroxy-1-acryloxy-3-methacryloxypropane, trimethylolpropane trimethacrylate, trimethylolpropane triacrylate, and tetramethylolmethane tetraacrylate. These compounds may be used alone, or two or more kinds thereof may be used in combination.

The amount of the crosslinking agent (C) varies depending on the desired crosslink density, the molecular weight of the anhydropolyamino acid (D) and the kind of radically activated polysaccharides (B), and can be appropriately selected, but is preferably within a range from 0.1 to 50% by weight, and more preferably from 1 to 40% by weight, based on the total number of monomer units of the main chain of the anhydropolyamino acid (D). In the present invention, the gel strength and the water absorbency of the water absorbent material can be controlled by using the crosslinking agent (C) in an amount within the above range.

As used herein, the term "crosslink density" means a ratio of a crosslinked moiety to the main chain of the polymer molecule. The crosslink density generally increases with an increase in the amount of the crosslinking agent (C), thus making it possible to enhance the gel strength of the water absorbent material. On the other hand, the crosslink density decreases with a decrease of the amount of the crosslinking agent (C), thus making it possible to enhance the water absorbency of the water absorbent material. In the present invention, the gel strength and the water absorbency of the water absorbent material can be controlled by selecting the crosslink density according to the purposes.

Typical method for producing the water absorbent material of the present invention will now be described.

The water absorbent material of the present invention can be produced by incorporating, as a main component, a water absorbent resin obtained by reacting a anhydropolyamino acid having an ethylenically unsaturated double bond (A) with polysaccharides (B), crosslinking the reaction product with a crosslinking agent (C) and hydrolyzing at least a portion of constituent components of the anhydropolyamino acid.

The reaction between the anhydropolyamino acid having an ethylenically unsaturated double bond (A) and the polysaccharides (B) can be preferably conducted by dissolving a anhydropolyamino acid having an ethylenically unsaturated double bond in the following solvent in the presence of an inert gas such as nitrogen.

The solvent is preferably an aprotic organic solvent such as dimethylformamide, dimethylacetamide, N-methyl-2-pyrrolidone, N,N'-dimethylimidazolinone, dimethyl sulfoxide, or sulfolane in view of good solubility of the anhydropolyamino acid (D).

In the case in which a portion or all of the anhydropolyamino acid having an ethylenically unsaturated double bond (A) is previously hydrolyzed, water can be used as the solvent.

When a anhydropolyamino acid (D) is reacted with a double bond-containing compound (E) for the purpose of introducing an ethylenically unsaturated double bond, in the case in which the reaction with the double bond-containing compound (E) is conducted in an aprotic organic solvent such as dimethylformamide, dimethylacetamide, N-methyl-2-pyrrolidone, N,N'-dimethylimidazolinone, dimethyl sulfoxide, or sulfolane, or is conducted in an aqueous solution by hydrolyzing or a portion or all of the anhydropolyamino acid (D), the reaction with the polysaccharides (B) can be conducted in a medium.

The reaction between a anhydropolyamino acid having an ethylenically unsaturated double bond (A) and polysaccharides (B) is initiated by dissolving or dispersing the polysaccharides (B) in a solution of the anhydropolyamino acid having an ethylenically unsaturated double bond (A) and adding a redox catalyst.

As the redox catalyst, namely water-soluble redox catalyst, an oxidizing agent, for example, persulfates such as ammonium persulfate and potassium persulfate, or peroxides such as hydrogen peroxide and hydroxy peroxide can be used in combination with an inorganic reducing agent (for example, $Fe^{2+}$ salt, bisulfite, ammonium sulfite, or ammonium bisulfite) or an organic reducing agent such as ascorbic acid. In the non-aqueous redox catalyst, an oxidizing agent such as hydroxy peroxide, dialkyl peroxide, diacyl peroxide, benzoyl peroxide, di-t-butyl peroxide, cumenhydroxy peroxide, succinic acid peroxide, or di(2-ethoxyethyl) peroxydicarbonate and a reducing agent, for example, organic compound such as tertiary amine, naphthenate, mercaptan, $Al(C_2H_5)_3$, $B(C_2H_5)_3$, or $Zn(C_2H_5)_2$ can be used. An acidic metal salt such as oxygen or cerium (tetravalent) salt, a halogen molecule such as $Cl_2$ or $Br_2$ and an organohalogen compound can be used in combination with a proper reducing agent.

The redox catalyst can be used in combination with a radical polymerization initiator. Examples of the radical polymerization initiator include azo compound [for example, azobisisobutyronitrile, azobiscyanovaleric acid, or 2,2'-azobis(2-amidinopropane) hydrochloride], in addition to peroxides described as the redox catalyst. These radical polymerization initiators may be used alone or in combination.

The amount of the redox catalyst is preferably within a range from 0.0001 to 5% by weight, and more preferably from 0.0005 to 1% by weight, based on the anhydropolyamino acid having an ethylenically unsaturated double bond (A).

The reaction temperature after the addition of the redox catalyst is preferably within a range from 0 to 300° C., and more preferably from 5 to 200° C.

A crosslinked compound can be obtained by the crosslinking reaction after the completion of the reaction.

The crosslinking reaction can be conducted in the same medium after the completion of the reaction between the anhydropolyamino acid having an ethylenically unsaturated double bond (A) and the polysaccharides (B). The reaction can also be conducted by adding the reaction product in a large amount of methanol, ethanol or acetone, thereby causing precipitation, or may be conducted in the absence of a solvent after isolation by drying with evaporating deionized water.

The method of adding the crosslinking agent (C) is not specifically limited and may be any method such as a method of adding as it is, method of adding by dissolving in a solvent, or method of adding in the form of a suspension.

The reaction temperature after the addition of the crosslinking agent (C) is preferably within a range from 0 to 300° C., and more preferably from 5 to 200° C.

The water absorbent material of the present invention can be obtained by hydrolyzing a portion or all of the crosslinked compound.

The hydrolysis reaction of the crosslinked compound is usually conducted by adding an aqueous alkali solution and the reaction temperature is preferably within a range from 0 to 100° C., and more preferably from 20 to 95° C.

The alkali metal compound and/or the alkali earth metal compound used in the hydrolysis of the crosslinked compound is preferably hydroxide or carbonate thereof, and examples thereof include lithium hydroxide, sodium hydroxide, potassium hydroxide, magnesium hydroxide, calcium hydroxide, lithium carbonate, sodium carbonate, potassium carbonate, magnesium carbonate, and calcium carbonate. Among these compounds, an aqueous solution (0.1 to 40% by weight) of sodium hydroxide or potassium hydroxide is preferably used. The amount of the alkali compound used in the hydrolysis of the crosslinked compound is preferably an amount corresponding to 0.4 to 1.0 mol based on 1 mol of the imide ring group.

The water absorbent material of the present invention is superior in both performances such as water absorbency and biodegradability.

The water absorbency can be determined by the water absorption test procedure (JIS K-7223) of a high water absorbent material described in the Japanese Industrial Standard. In the case of evaluating by the tea bag method, the water absorbent material of the present invention has a water absorbency 20 times or more for deionized water, or a water absorbency of 5 times or more for physiological saline (0.9 wt % aqueous sodium chloride solution).

Furthermore, the water absorbent material of the present invention is decomposed merely by burying it in the ground because of its biodegradability capable of being decomposed by bacteria or microorganisms in the ground. Therefore, it does not cause environmental sanitation problems such as environmental pollution because of simple disposal and excellent safety.

The water absorbent material of the present invention can be used for various purposes which have been conventionally known. For example, it is employed in various fields, for example, in sanitation fields such as for sanitary material products (disposable diapers and sanitary napkins); in medical fields such as for wet compresses; in civil engineering and construction fields such as for sludge gelling agents; in the field of foods; in the industrial field; and in agricultural/horticultural fields such as for soil conditioning and water-storing materials; and its utility value is great.

The water absorbent article of the present invention will now be described.

The water absorbent article of the present invention comprises a liquid permeable sheet, a liquid impermeable sheet, and a water absorber containing a water absorbent material and a fiber material, which is formed between the liquid permeable sheet and the liquid impermeable sheet, wherein the water absorbent material used is a water absorbent material comprising, as a main component, a water absorbent resin which has a structure in which a anhydropolyamino acid having an ethylenically unsaturated double bond is grafted with polysaccharides, wherein at least a portion of the anhydropolyamino acid is hydrolyzed and crosslinked.

The liquid permeable sheet constituting the water absorbent article of the present invention means a sheet made of a material having a property which permeates an aqueous liquid and includes, for example, a film made of a material such as nonwoven fabric, woven fabric, polyethylene, polypropylene, or polyamide.

The liquid impermeable sheet constituting the water absorbent article of the present invention means a sheet having a property which does not allow permeation of an aqueous liquid, and includes, for example, synthetic film made of a material such as polyethylene, polypropylene, ethylene vinyl acetate, or polyvinyl chloride, or film made of a composite of the synthetic resin and a nonwoven fabric or a woven fabric. This liquid impermeable sheet may have a property which allows permeation of water vapor therethrough.

As the water absorbent material constituting the water absorbent article of the present invention, the water absorbent material described above can be used.

Examples of the fiber material constituting the water absorbent article of the present invention include hydrophobic fiber material and hydrophilic fiber material, and the hydrophilic fiber material is preferred in view of excellent affinity with the liquid to be absorbed. Examples of the affinitive fiber material include cellulose fibers obtained from wood, such as mechanical pulp and chemical pulp; artificial cellulose fibers such as rayon and acetate; and fiber materials obtained by hydrophilizing a thermoplastic resin.

The form of the fiber material is not specifically limited and, for example, a sheet such as tissue paper or pulp mat can be appropriately selected.

The water absorbent article of the present invention is obtained by forming an absorber containing the water absorbent material and the fiber material between the liquid permeable sheet and the liquid impermeable sheet, and has a structure comprising the absorber therein.

The method for producing the absorbent article is specifically a method of sandwiching the absorber between liquid permeable sheet and the liquid impermeable sheet and bonding the liquid permeable sheet with an outer periphery of the liquid impermeable sheet using an adhesive such as hot melt adhesive or a bonding means such as a heat seal.

The method for producing the absorber containing the water absorbent material and the fiber material is not specifically limited, and examples thereof include (1) method of forming a fiber material into a sheet and covering the water absorbent material with the sheet, (2) method of scattering a water absorbent material over a multi-layer fiber sheet and forming the multi-layer fiber sheet, and (3) method of mixing a fiber material with a water absorbent material and forming the mixture into a sheet.

The water absorbent article of the present invention can be employed in various fields, for example, in fields of sanitary products such as for disposable diapers for infants, adults, or persons suffering from incontinence, or for sanitary napkins; in medical fields such as for wet compresses; in civil engineering and construction fields such as for sludge gelling agents, soil conditioners, and sealing materials; in transportation of fresh food or seafood; in industrial fields such as for solvent dehydrating agents; and in agricultural/horticultural fields, because of excellent absorbency of urea or body fluids and excellent liquid leakage inhibition effects, and its utility value is great.

EXAMPLES

The following Examples further illustrate the present invention, but the present invention is not limited by the Examples. In the Examples, percentages are by weight unless otherwise specified. Various characteristics of the resin of the present invention were determined by the following procedures.

Method of Measuring Water Absorption Ratio

The water absorbency of the resins obtained in the Examples and Comparative Example was measured in accordance with the water absorption test procedure of a high water absorbent material described in Japanese Industrial Standard JIS K-7223. 0.20 g of a dry resin (1.00 g based on an aqueous 0.9% sodium hydroxide solution) was charged in a 255 mesh tea bag made of a nylon gauze (200 mm×100 mm) and dipped in 1000 ml of deionized water or an aqueous 0.9% sodium chloride solution, thereby to swell the resin for a fixed time. After pulling up the tea bag, the solution was drained for 10 minutes and the weight of the resin was measured. The same operation was repeated, except that only the tea bag was used, and the weight of the resin was measured as a blank. The water absorption ratio W (g/g) was calculated according to the following equation:

$$W = \frac{b-c-a}{a}$$

where 'a' denotes a weight (g) of sample, 'b' denotes a weight (g) after a tea bag contaning the sample was dipped for a predetermined time and water was drained, and 'c' denotes a weight (g) after a tea bag contaning no sample was dipped for a predetermined time and water was drained.

Synthesis Example 1

In a 2 L Kjeldahl flask, 100 g of L-aspartic acid and 50 g of 85% phosphoric acid were charged and then reacted under reduced pressure in an oil bath at a bath temperature of 200° C. for 4 hours using an evaporator. 25 g of the resulting product was washed several times with water and methanol to obtain imide polysuccinate. The molecular weight was measured by gel permeation chromatography (hereinafter referred to as GPC). As a result, the weight-average molecular weight (hereinafter referred to as Mw) of imide polysuccinate was 20,000.

Synthesis Example 2

In a 1 L four-necked flask equipped with a stirrer, a thermometer, a refluxing device, and a nitrogen gas introducing device, 96 g of maleic anhydride and 50 g of deionized water were charged and heated to 55° C., thereby to dissolve maleic anhydride, followed by cooling to obtain a slurry of maleic anhydride. After heating the system again, 60.8 g of 28% ammonia water was added when the temperature reached 55° C. The system was heated to 80° C. and, after reacting for 3 hours, the resulting aqueous solution was dried to obtain a reaction intermediate. In a 2 L Kjeldahl flask, 100 g of the reaction intermediate and 10 g of 85% phosphoric acid were charge and this was then reacted under reduced pressure in an oil bath at a bath temperature of 200° C. for 4 hours using an evaporator. The resulting product was washed several times with water and methanol to obtain imide polysuccinate. Mw of imide polysuccinate was measured by GPC. As a result, it was 3,000.

Example 1

In a 500 ml four-necked flask equipped with a stirrer, a thermometer, a refluxing device and a nitrogen gas introducing device, 60 g of dimethyl sulfoxide was charged and then dissolved by adding 30 g of imide polysuccinate obtained in Synthesis Example 1. Then, a solution of imide polysuccinate having a methacrylate group introduced therein was obtained by bubbling air into a liquid for 15 minutes, adding 3 g of 2-methacryloyloxyethyl isocyanate (manufactured by Showa Denko K. K. under the trade name of Karenz MOI), raising the internal temperature to 70° C. and reacting for 2 hours.

After 30 g of carboxymethylated starch (manufactured by Nippon Starch Chemical Co., Ltd., under the trade name of Kiprogum F-500) was added and dispersed in the resulting solution of imide polysuccinate having a methacrylate group introduced therein while stirring, 0.05 g of ascorbic acid, 0.575 g of 35% hydrogen peroxide water and 0.01 g of azobisisobutyronitrile were added and mixed. The internal temperature was raised to 60° C. and the reaction was conducted for 3 hours. After the completion of the reaction, the solution was washed several times with methanol, the precipitated solid was vacuum-dried at 120° C. to obtain 55.8 g of a white powder.

In a 100 ml erlenmeyer flask, 0.30 g of 1,8-diaminooctane was charged and 8 g of methanol were added to obtain a solution of a crosslinking agent. To the solution, 8 g of the white powder obtained by the operation described above was added and, after uniformly stirring using a stirring bar and being held in a water bath having a bath temperature of 70° C. for 2 hours, the temperature was once returned to room temperature. Then, 15 g of an aqueous sodium hydroxide solution prepared by dissolving 1.25 g of sodium hydroxide was added and the solution was uniformly stirred again using a stirring bar. The resulting solid was washed several times with methanol and was then vacuum-dried at 120° C. to obtain a water absorbent material of the present invention. The composition of the raw materials used in the reaction is shown in Table 1-1 and the evaluation results of characteristics of the resulting water absorbent material of the present invention are shown in Table 2.

Comparative Example 1

In a 100 ml erlenmeyer flask, 0.59 g of 1,8-diaminooctane was charged and 10 g of methanol was added to obtain a solution of a crosslinking agent. To the solution, 8 g of imide polysuccinate obtained in Synthesis Example 1 was added and, after uniformly stirring using a stirring bar and being held in a water bath having a bath temperature of 70° C. for 2 hours, the temperature was once returned to room temperature. Then, 10 g of an aqueous sodium hydroxide solution prepared by dissolving 2.51 g of sodium hydroxide was added and the solution was uniformly stirred again using a stirring bar. The resulting solid was washed several times with methanol and was then vacuum-dried at 120° C. to obtain a water absorbent material of the present invention. The composition of the raw materials used in the reaction is shown in Table 1-2 and the evaluation results of characteristics of the resulting reaction product of the present invention are shown in Table 2.

Example 2

In a 500 ml four-necked flask equipped with a stirrer, a thermometer, a refluxing device and a nitrogen gas introducing device, 40 g of dimethyl sulfoxide was charged and then dissolved by adding 40 g of imide polysuccinate obtained in Synthesis Example 2. After air was bubbled into the liquid for 15 minutes and 4 g of 2-methacryloyloxyethyl isocyanate was added, the same operation as in Example 1 was conducted, except that the amount of the carboxymethylated starch was changed to 40 g, and 64.3 g of a brown powder was obtained.

In a 100 ml erlenmeyer flask, 1.5 g of 1,8-diaminooctane was charged and 10 g of methanol was added to obtain a solution of a crosslinking agent. The same operation as in Example 1 was conducted, except that 8 g of the brown powder obtained by the above operation was added to the solution and 10 g of an aqueous sodium hydroxide solution prepared by dissolving 1.23 g of sodium hydroxide was added, a water absorbent material of the present invention was obtained. The composition of the raw materials used in the reaction is shown in Table 1-1 and the evaluation results of characteristics of the resulting water absorbent material of the present invention are shown in Table 2.

Example 3

The same procedure as in Example 2 was conducted, except that the carboxymethylated starch was replaced by a pregelatinized starch (manufactured by Nippon Starch Chemical Co., Ltd. under the trade name of AMYCOL HF), and 58.1 g of a brown powder was obtained.

In a 100 ml erlenmeyer flask, 0.49 g of ethylenediamine was charged and 10 g of methanol was added to obtain a solution of a crosslinking agent. The same operation as in Example 1 was conducted, except that 8 g of the brown powder obtained by the above operation was added and 10 g of an aqueous sodium hydroxide solution prepared by dissolving 1.32 g of sodium hydroxide was added, a water absorbent material of the present invention was obtained. The composition of the raw materials used in the reaction is shown in Table 1-1 and the evaluation results of characteristics of the resulting water absorbent material of the present invention are shown in Table 2.

Example 4

The same operation as in Example 1 was conducted, except that 0.49 g of ethylenediamine was replaced by 0.41 g of 80% hydrated hydrazine in Example 3, and a water absorbent material of the present invention was obtained. The composition of the raw materials used in the reaction is shown in Table 1-1 and the evaluation results of characteristics of the resulting water absorbent material of the present invention are shown in Table 2.

Comparative Example 2

In a 100 ml erlenmeyer flask, 1.4 g of hexamethylenediamine was charged and 10 g of methanol was added to obtain a solution of a crosslinking agent. To the solution, 8 g of imide polysuccinate obtained in Synthesis Example 2 was added and, after uniformly stirring using a stirring bar and being held in a water bath having a bath temperature of 70° C. for 2 hours, the temperature was once returned to room temperature. Then, 10 g of an aqueous sodium hydroxide solution prepared by dissolving 2.80 g of sodium hydroxide was added and the solution was uniformly stirred again using a stirring bar. The resulting solid was washed several times with methanol and was then vacuum-dried at 120° C. to obtain a water absorbent material of the present invention. The composition of the raw materials used in the reaction is shown in Table 1-2 and the evaluation results of characteristics of the resulting reaction product of the present invention are shown in Table 2.

Comparative Example 3

The same operation as in Comparative Example 2 was conducted, except that the amount of hexamethylenediamine was replaced by 2.9 g and the amount of sodium hydroxide was replaced by 2.31 g in Comparative Example 2, and a reaction product was obtained. The composition of the raw materials used in the reaction is shown in Table 1-2 and the evaluation results of characteristics of the resulting reaction product of the present invention are shown in Table 2.

Comparative Example 4

In a 500 ml four-necked flask equipped with a stirrer, a thermometer, a refluxing device and a nitrogen gas introducing device, 40 g of imide polysuccinate obtained in Synthesis Example 2, 40 g of pregelatinized starch and 40 g of dimethyl sulfoxide were charged and dissolved by heating to 60° C. for 3 hours. The resulting solution was washed several times with methanol and the precipitated solid was vacuum-dried at 120° C. to obtain 47.8 g of a white powder.

In a 100 ml erlenmeyer flask, 0.49 g of ethylenediamine was charged and 10 g of methanol was added to obtain a solution of a crosslinking agent. The same operation as in Example 1 was conducted, except that 8 g of the brown powder obtained by the above operation was added and 10 g of an aqueous sodium hydroxide solution prepared by adding 1.32 g of sodium hydroxide was added, and a reaction product was obtained. The composition of the raw materials used in the reaction is shown in Table 1-2 and the evaluation results of the characteristics of the resulting reaction product of the present invention are shown in Table 2.

Comparative Example 5

The same operation as in Comparative Example 4 was conducted, except that 10 g of an aqueous sodium hydroxide solution prepared by dissolving 1.2 g of ethylenediamine and 0.82 g of sodium hydroxide was added, and a reaction product was obtained. The composition of raw materials used in the reaction is shown in Table 1-2 and the evaluation results of characteristics of the resulting reaction product are shown in Table 2.

TABLE 1-1

| Charge composition (g) | Example 1 | Example 2 | Example 3 | Example 4 |
|---|---|---|---|---|
| Step 1 (introduction of methacrylate group and reaction between PSI and polysaccharides) | | | | |
| PSI 1 (product in Synthesis Example 1) | 30 | — | — | — |
| PSI 2 (product in Synthesis Example 2) | — | 40 | 40 | 40 |
| DMSO | 60 | 40 | 40 | 40 |
| 2-MOI | 3 | 4 | 4 | 4 |
| Carboxymethylated starch | 30 | 40 | — | — |
| Pregelatinized starch | — | — | 40 | 40 |
| Ascorbic acid | 0.05 | 0.05 | 0.05 | 0.05 |
| 35% hydrogen peroxide water | 0.575 | 0.575 | 0.575 | 0.575 |
| AIBN | 0.01 | 0.01 | 0.01 | 0.01 |
| Step 2 (crosslinking reaction and hydrolysis reaction) | | | | |
| Solid produced in step 1 | 8 | 8 | 8 | 8 |
| PSI 1 (product in Synthesis Example 1) | — | — | — | — |
| PSI 2 (product in Synthesis Example 2) | — | — | — | — |
| 1, 8-diaminooctane | 0.30 | 1.5 | — | — |
| Hexamethylenediamine | — | — | — | — |
| Ethylenediamine | — | — | 0.49 | — |
| 80% hydrated hydazine | — | — | — | 0.41 |
| Methanol | 8 | 10 | 10 | 10 |
| Sodium hydroxide | 1.25 | 1.23 | 1.32 | 1.32 |
| Deionized water | 13.8 | 9.21 | 8.68 | 8.68 |

TABLE 1-2

| | Comp. Example 1 | Comp. Example 2 | Comp. Example 3 | Comp. Example 4 | Comp. Example 5 |
|---|---|---|---|---|---|
| Step 1 (introduction of methacrylate group and reaction between PSI and polysaccharides) | | | | | |
| PSI 1 (product in Synthesis Example 1) | — | — | — | — | — |
| PSI 2 (product in Synthesis Example 2) | — | — | — | 40 | 40 |
| DMSO | — | — | — | 40 | 40 |
| 2-MOI | — | — | — | — | — |
| Carboxymethylated starch | — | — | — | — | — |
| Pregelatinized starch | — | — | — | 40 | 40 |
| Ascorbic acid | — | — | — | — | — |
| 35% hydrogen peroxide water | — | — | — | — | — |
| AIBN | — | — | — | — | — |
| Step 2 (crosslinking reaction and hydrolysis reaction) | | | | | |
| Solid produced in step 1 | — | — | — | 8 | 8 |
| PSI 1 (product in Synthesis Example 1) | 8 | — | — | — | — |
| PSI 2 (product in Synthesis Example 2) | — | 8 | 8 | — | — |
| 1, 8-diaminooctane | 0.59 | — | — | — | — |
| Hexamethylenediamine | — | 1.4 | 2.9 | — | — |
| Ethylenediamine | — | — | — | 0.49 | 1.2 |
| 80% hydrated hydazine | — | — | — | — | — |
| Methanol | 10 | 10 | 10 | 10 | 10 |

TABLE 1-2-continued

|  | Comp. Example 1 | Comp. Example 2 | Comp. Example 3 | Comp. Example 4 | Comp. Example 5 |
|---|---|---|---|---|---|
| Sodium hydroxide | 2.51 | 2.80 | 2.31 | 1.32 | 0.82 |
| Deionized water | 7.49 | 7.20 | 7.69 | 8.68 | 9.18 |

Abbreviations in Table 1 are as follows.
PSI 1: imide polysuccinate obtained in Synthesis Example 1
PSI 2: imide polysuccinate obtained in Synthesis Example 2
DMSO: dimethyl sulfoxide
2-MOI: 2-methacryloyloxyethyl isocyanate
AIBN: azobisisobutyronitrile

TABLE 2

Evaluation results

Water absorption ratio (%)

| | Deionized water (g/g) | 0.9% physiological saline (g/g) |
|---|---|---|
| Example 1 | 188 | 47 |
| Comp. Example 1 | 38 | 11 |
| Example 2 | 91 | 25 |
| Example 3 | 63 | 18 |
| Example 4 | 86 | 23 |
| Comp. Example 2 | Dissolved | Dissolved |
| Comp. Example 3 | 8 | 3 |
| Comp. Example 4 | Dissolved | Dissolved |
| Comp. Example 5 | 21 | 8 |

What is claimed is:

1. A water absorbent material comprising, as a main component, a water absorbent resin which has a structure in which a anhydropolyamino acid having an ethylenically unsaturated double bond is grafted with polysaccharides, wherein at least a portion of the anhydropolyamino acid is hydrolyzed, and crosslinked.

2. A water absorbent material according to claim 1, wherein the water absorbent resin is obtained by reacting a anhydropolyamino acid having an ethylenically unsaturated double bond (A) with polysaccharides (B), crosslinking the reaction product with a crosslinking agent (C), and hydrolyzing at least a portion of constituent components of the anhydropolyamino acid.

3. A water absorbent material according to claim 2, wherein the water absorbent resin is obtained by reacting the anhydropolyamino acid having an ethylenically unsaturated double bond (A) with the polysaccharides (B) in the presence of a redox catalyst, crosslinking the reaction product with the crosslinking agent (C), and hydrolyzing at least a portion of constituent components of the anhydropolyamino acid.

4. A water absorbent material according to claim 2, wherein the anhydropolyamino acid having an ethylenically unsaturated double bond (A) is a reaction product of a anhydropolyamino acid (D) and a compound (E) which has an ethylenically unsaturated double bond and a functional group having a reactivity with the anhydropolyamino acid (D) in a molecule.

5. A water absorbent material according to claim 2, wherein the compound (E) which has an ethylenically unsaturated double bond and a functional group having a reactivity with the anhydropolyamino acid (D) in a molecule is a compound represented by the following general formula (1):

General Formula (1)

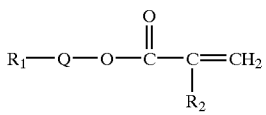

wherein $R_1$ represents at least one functional group selected from the group consisting of amino groups, epoxy groups, carboxyl groups, carbodiimide groups, oxazoline groups, imino groups, and isocyanate groups, Q represents an alkylene group having 1 to 10 carbon atoms, and $R_2$ represents hydrogen or an alkyl group having 1 to 4 carbon atoms.

6. A water absorbent material according to claim 2, wherein the anhydropolyamino acid (D) is imide polysuccinate.

7. A method for producing a water absorbent material comprising a water absorbent resin as a main component, which comprises reacting a anhydropolyamino acid having an ethylenically unsaturated double bond (A) with polysaccharides (B), crosslinking the reaction product with a crosslinking agent (C), and hydrolyzing at least a portion of constituent components of the anhydropolyamino acid.

8. A water absorbent article comprising a liquid permeable sheet, a liquid impermeable sheet, and a water absorber containing a water absorbent material and a fiber material, which is formed between the liquid permeable sheet and the liquid impermeable sheet, wherein the water absorbent material used is a water absorbent material comprising, as a main component, a water absorbent resin which has a structure in which a anhydropolyamino acid having an ethylenically unsaturated double bond (A) is grafted with polysaccharides, wherein at least a portion of the anhydropolyamino acid is hydrolyzed and crosslinked.

* * * * *